United States Patent [19]
Watt et al.

[11] 4,090,074
[45] May 16, 1978

[54] ANALYSIS OF COAL

[75] Inventors: John Stanley Watt, Heathcote; Vilis Leonids Gravitis, Revesby, both of Australia

[73] Assignee: Australian Atomic Energy Commission, Coogee, Australia

[21] Appl. No.: 732,644

[22] Filed: Oct. 15, 1976

[30] Foreign Application Priority Data

Oct. 29, 1975  Australia .............................. 3760/75

[51] Int. Cl.² .......................................... G01N 23/20
[52] U.S. Cl. ................................. 250/273; 250/358 R
[58] Field of Search ............... 250/253, 255, 272, 273, 250/358 R

[56] References Cited
U.S. PATENT DOCUMENTS

| 3,270,204 | 8/1966 | Rhodes | 250/272 |
| 3,361,911 | 1/1968 | Kowalczynski | 250/272 |

*Primary Examiner*—Davis L. Willis
*Attorney, Agent, or Firm*—Haseltine, Lake & Waters

[57] ABSTRACT

A method of analysing coal or coke wherein the concentration of ash or mineral matter in coal or coke is determined from (i) the result of a measurement of transmission or scatter of X-rays or γ-rays of a first energy chosen such that there is significant difference in absorption of radiation per unit weight in coal matter and mineral matter excluding iron, combined with (ii) the result of at least one further measurement of transmission or scatter of X-rays or γ-rays at different energy/energies so chosen that there is significant difference in absorption of radiation per unit weight of coal matter and mineral matter and that the relative absorption per unit weights by said coal matter and said mineral matter at any one energy is significantly different from the relative absorption at each other energy including said first energy, and/or (iii) the result of a measurement of iron concentration by neutron capture γ-ray techniques.

15 Claims, 3 Drawing Figures

ANALYSIS OF COAL

FIELD OF THE INVENTION

The present invention relates to the determination of the ash content of coal or coke employing measurements from X-rays, γ-rays and/or neutrons.

BACKGROUND

An accurate knowledge of the composition of coal or coke is very important in many aspects of production or beneficiation and in the utilisation of coal or coke in order to ensure a uniform product and/or batch.

Coal and coke consists of coal matter (oxygen and combustible materials, carbon, hydrogen and a little nitrogen and sulphur) and mineral matter (mainly of incombustible aluminium and other silicates, and a little iron sulphide which is partly combustible). Coal ash is the oxidised incombustible residue from the combustion of coal, and is closely correlated with the content of mineral matter.

An accurate knowledge of the mineral content of coal is very important in many aspects of coal production, preparation and utilisation. It is especially advantageous to have a continuous monitor of mineral content of coal during coal washing and blending operations, production of coke, and monitoring feed in installations for power generation, metallurgical smelting and gas production.

Coal as mined has a variable heterogeneous mineralogy and usually a wide particle size distribution. The coal is washed to reduce mineral content and to ensure a more uniform product, and blended to obtain specific characteristics suitable for a particular application requirement. When the mineral content can be monitored continuously, washing and blending can be controlled better to ensure a more uniform and lower mineral content and therefore more appropriate characteristics.

In the specification and claims when describing methods of determining ash content of coal a reference to coal is also a reference to coke. Also, since the content of mineral matter is closely related to the content of ash, the content of one can be determined at least approximately from a measurement of the other.

It is known to determine the ash content of coal gravimetrically by burning a known amount of coal and weighing the residue. In order to reduce errors, a large sample is taken and ground and the sample size reduced in accordance with standard sampling procedures. This method does not permit a rapid continuous monitor of ash content.

Continuous and rapid methods for determining the ash content of coal are known and depend on scatter of β particles, or transmission or scatter of X- or γ-rays. Such methods are described in Cameron J. F., "Measurement of ash content and calorific value of coal with radioisotope instruments" O.R.N.L. 11C-10 Vol. 2 P 903, Cameron J. F., Clayton C. G., "Radioisotope Instruments Volume 1" International Series of Monographs in nuclear energy Volume 107, Pergamon Press (1971), Kato M., "Present status of research and application of low-energy X-and gamma-ray sources in Japan" O.R.N.L. 11C-10 Vol. 2 P 723, Rhodes J. R., "Ore and Coal Analyses using radioisotope techniques" O.R.N.L. 11C-5, P 206 and Vasilev A. G. et al, "Express ash analyser based on the recording of forward scattered gamma rays" Koksi Khimiya 1974 No. 5, P 52. The basis of these methods is that the mean atomic number of the mineral matter constituents is higher than that of the coal matter, and that β and γ-ray interactions with atoms are atomic number dependent. The mean atomic number of mineral matter, however, is not constant, and in practice variations in iron content of the mineral matter cause considerable errors in determination of ash using the above methods.

Neutron techniques can, in principle, be used to determine ash content of coal because these techniques can be used to determine concentrations of the more abundant elements of the coal. Such methods are described in Cameron J. F., "Measurement of ash content and calorific value of coal with radioisotope instruments" O.R.N.L. 11C-10 Vol. 2 P 903. Neutrons, and the γ-rays produced by neutron interactions with the coal, both penetrate large volumes of coal and hence neutron techniques can be used with relatively large particles of coal. However, determination of concentrations of all the elements required for accurate determination of ash content would, in practice, be very complex because some of the neutron techniques for individual elements are complex. Techniques are, in practice, relatively simple for only a limited number of elements, e.g., iron by neutron capture γ-ray techniques as described by FMC Corporation, "Analysis of coal with Cf-252", pages 37 to 39 in Californium Progress, Jan. 20, 1976 and by Ljunggren K. and Christell R., "On-line determination of the iron content of ores, ore products and wastes by means of neutron capture gamma radiation measurement", page 181 in Nuclear Techniques in Geochemistry and Geophysics, IAEA, Vienna 1976.

In methods based on scatter of β particles, the intensity of particles scattered from a material is related to the mean atomic number of the material. As the mean atomic number of coal increases with mineral matter content the intensity of β particles scattered from coal is proportional to the ash content. However, large errors occur in this method through variations in iron and moisture content.

In methods based on transmission of X-rays or low energy γ-rays the intensity of the radiation transmitted through a sample of fixed weight per unit area decreases with increasing mass attenuation coefficient of the bulk material. At energies less than about 100 keV the mass attenuation coefficient changes rapidly with atomic number, which means that the transmitted intensity is sensitive to the coal composition.

The ratio of the intensity (I) of a collimated beam of radiation transmitted through a coal sample of thickness (x) and bulk density (ρ) to the intensity ($I_o$) in the absence of coal is $$I/I_0 = \exp(-(\Sigma \mu_i C_i) \rho \cdot x) \quad (1)$$

where $\mu_i$ and $C_i$ are the mass absorption coefficient and concentration (weight fraction) of the $i^{th}$ element in the coal respectively. Now $$\Sigma \mu_i C_i = \mu_{coal\ matter} \cdot C_{coal\ matter} + \mu_{mineral\ matter} \cdot C_{mineral\ matter} \quad (2)$$

where C is concentration and $$C_{coal\ matter} + C_{mineral\ matter} = 1 \quad (3)$$

Hence if coal samples to be analysed have mineral matter of essentially constant composition and if the weight per unit area (ρ·x) of coal is separately measured, and results combined with equations (1), (2) and (3), the concentration of mineral matter and hence the closely correlated ash content are determined.

A high sensitivity to variations in mineral matter content can be obtained with methods employing transmission because the sensitivity to content of mineral matter is proportional to $(x)$ in equation (1).

In methods based on scatter of X- or $\gamma$-rays, the intensity (I) of radiation scattered from the coal depends on the probability of coherent and Compton scattering, and absorption of X- or $\gamma$-rays, within the sample. The optimum energy range for maximum sensitivity to ash is 10 to 20 keV, and in this case $$I \approx k/\Sigma(\mu_i C_i) \qquad (4)$$

wherein $\mu_i$ and $C_i$ are the mass absorption coefficient and concentration respectively for the $i^{th}$ element in the coal sample, and $k$ depends on overall geometry and detection efficiency, and output of the $\gamma$- or X-ray source. If coal samples to be analysed have mineral matter of essentially constant chemical composition, then mineral matter content and the closely correlated ash content are determined.

Variations in iron content of the mineral matter affect both the X- and $\gamma$-ray transmission and scatter methods as follows:

(1) If the X-ray energies are chosen below the iron K shell absorption edge (7,1 keV), the mass absorption coefficient of iron and the mean for the other constituents of mineral matter is about the same and the mineral matter content and hence ash is determined with reasonable accuracy. However, these low energy X-rays are strongly absorbed and the coal must be finely ground (less than 0,3 mm) so that measurements can be made. This is a severe limitation in practice for on-line determination.

(2) If the X-ray energies are chosen above the iron K shell absorption edge, compensation must be made for iron content because iron absorbs far more per unit weight than the absorption per unit weight of the other constituents of the mineral matter. The only compensation currently used for iron depends on excitation of iron K X-rays. This method can only be used on finely ground coal since the K X-rays are greatly absorbed in less than 1 mm thickness of coal.

Hence, unless the very unusual case occurs of essentially no variation of iron content of the mineral matter, the content of mineral matter and hence ash can only be determined accurately by currently used $\gamma$-ray and X-ray techniques if the particle size of coal is very small.

It would be expected therefore from the prior art that accurate determination of ash content of coal by X-ray and low energy $\gamma$-ray techniques would be unlikely unless the iron content of the ash was constant or the coal particles were finely ground. It would also be expected from prior art that the use of neutron techniques to determine ash content accurately would not be a practical proposition particularly for on-line systems.

SUMMARY OF THE INVENTION

The method of the present invention determines ash content even when the iron concentration varies and can be used on relatively large diameter coal particles.

According to the invention the concentration of ash or mineral matter in coal or coke is determined from (i) the result of a measurement of transmission or scatter of X-rays or $\gamma$-rays of a first energy chosen such that there is significant difference in absorption of radiation per unit weight in coal matter and mineral matter excluding iron, combined with (ii) the result of at least one further measurement of transmission or scatter of X-rays or $\gamma$-rays at different energy/energies so chosen that there is a significant difference in absorption of radiation per unit weight of coal matter and mineral matter and that the relative absorption per unit weights by said coal matter and said mineral matter at any one energy is significantly different from the relative absorption at each other energy, and/or (iii) the result of a measurement of iron concentration by neutron capture $\gamma$-ray techniques.

In this specification and claims the term "low energy $\gamma$-rays" means $\gamma$-rays of such an energy that the absorption of radiation per unit weight of at least some elements is significantly different from the absorption per unit weight of other elements.

In a first form of the invention the concentration of ash or mineral matter in coal or coke is determined from the result of a measurement of transmission or scatter of X-rays or $\gamma$-rays of a first energy chosen such that there is significant difference in absorption of radiation per unit weight in coal matter and mineral matter excluding iron, combined with the result of a second measurement of transmission or scatter of X-rays or $\gamma$-rays at a second energy chosen that the absorption of radiation per unit weight of mineral matter is significantly different from that of coal matter and that the relative absorption per unit weights by said mineral matter and said coal matter at said first energy is significantly different from the relative absorption at said second energy.

In a second form of the invention the concentration of ash or mineral matter in coal or coke is determined from the result of a measurement of iron concentration by neutron capture $\gamma$-ray techniques combined with the measurement of transmission or scatter of X-rays or $\gamma$-rays at an energy chosen such that there is a significant difference in absorption of radiation per unit weight in coal matter and mineral matter excluding iron.

In a third form of the invention the concentration of ash or mineral matter in coal or coke is determined from the results as described above in the first form of the invention combined with the result of a measurement of iron concentration by neutron capture $\gamma$-ray techniques.

In applying the method of the invention, the concentration of mineral matter is normally determined by the aforementioned measurements coupled with one or more additional measurements selected from (i) measurement of weight per unit area or a measurement proportional thereto, or (ii) measurement of bulk density. Usually, only one of these two measurements is required.

In one case the ash content may be determined by the two scatter measurements of X- or low energy $\gamma$-rays at different energies alone wherein the geometry of source, sample and detector is chosen so that the scattered intensity for both beams is essentially independent of bulk density of the coal or is affected proportionately the same by changes in bulk density.

Where the moisture content of the coal or hydrogen content of the coal matter varies considerably the ash content of coal can be determined more accurately by combining the method of the invention with a measurement of moisture or hydrogen content. Methods of measuring moisture and hydrogen in coal are known γ-rays to determine both iron and hydrogen content of the coal is shown in FIG. 3. The neutrons and γ-rays interact with coal 1 on a conveyor belt 2. The neutron source 17 of californium-252, plutonium-238/beryllium, or americium-241/beryllium is contained in a neutron shielding material 18 open at the end facing the conveyor belt. Neutrons are absorbed by hydrogen and iron in the coal, and the resulting capture γ-rays from hydrogen (energy 2,23 MeV) and iron (energy approximately 7,6 MeV) are detected by scintillation detector 19 which is shielded by a thermal neutron shield 20, e.g., boron. A γ-ray shield 15 is placed between neutron source 17 and scintillation detector 19 to shield the detector from γ-rays emitted by the neutron source. The high energy γ-rays are provided by a barium-133 radioisotope source 20 which emits γ-rays at 356 KeV and other energies and these γ-rays are detected by scintillation detector 7. This γ-ray beam is collimated by γ-ray shields 3. The low energy γ-rays are provided by an americium-241 radioisotope source 21 and after scattering in the coal the resultant γ-rays are detected by scintillation detector 7'. This low energy γ-ray beam is partly collimated by γ-ray shields 3', and a further shield 15' may be used depending mainly on the thickness of the coal layer.

The electronics used with the scintillation detectors 19, 7, 7' are known art and comprise high voltage units 8 to polarise the scintillation detectors 19, 7, 7', amplifiers 9, discriminators 11 to differentiate signal from noise and analogue-to-digital converter 22, and interface units 12 to link the outputs from units 11, 22 with the digital computer 13. The analogue-to-digital converter 22 used in conjunction with the computer 13 enables the γ-ray spectra from scintillation detector 19 to be processed so that the intensities of hydrogen capture γ-rays and iron capture γ-rays can be determined. The computer combines the signals and calculates the ash content.

In the above examples, mechanical devices to improve consistency of weight per unit area of coal seen by the radiation beams may improve the accuracy of analysis for ash content. The intensity of X- and γ-rays measured by each scintillation detector should be converted to logarithmic form in times sufficiently short to ensure that changes in intensity during the time are small.

The method of the invention has been proved in the experimental determination of the ash content of run-of-the mine coal samples taken from 12 different collieries operating on the Bulli coal seam, N.S.W., Australia. The ash content of the samples varied in the range of 11 to 25 wt.%, with a mean of 17,6 wt.%. Measurements were made of the transmissions of silver $K_\alpha$ X-rays (energy 22 keV), cerium $K_\alpha$ X-rays (35 keV), and barium-133 γ-rays (356 keV) through the coal samples. The transmitted X-ray intensities were measured using a germanium solid state detector, and the barium-133 γ-ray intensity was measured using a collimated scintillation detector.

The equation used to combine the measurements of intensities of X- and γ-rays was:

$$C_{ash} = \frac{a_1 \log(\frac{I}{I_o})_{22} + a_2 \log(\frac{I}{I_o})_{35}}{\log(\frac{I}{I_o})_{356}} + a_3$$

where $C_{ash}$ is the concentration of ash in the coal, $I$ and $I_o$ are respectively the measured intensities of X- or γ-rays with and without coal present, subscripts 22, 35, and 356 refer to the approximate energy of the X- or γ-rays measured and $a_1$, $a_2$ and $a_3$ are constants determined by least squares regression analysis using the measured X- and γ-ray intensities and the ash assay as determined by the conventional technique used in the coal industry.

The standard error was 0,67 wt.% ash, and the correlation coefficient 0,995. The standard error from least squares regression analysis using ash content and intensities of silver $K_\alpha$ X-rays and barium-133 γ-rays only was 1,61 wt.%. The reduction in standard error from 1,61 to 0,67 wt.% ash when the cerium $K_\alpha$ X-ray intensity is also used, demonstrates that the method of the invention compensates well for changes in ash composition.

What we claim is:

1. A method of analyzing coal or coke comprising determining the concentration of ash or mineral matter in coal or coke by the steps comprising (i) measuring the transmission or scatter of X-rays or γ-rays of a first energy chosen such that there is significant difference in absorption of radiation per unit weight in coal matter and mineral matter excluding iron, in combination with (ii) effecting at least one further measurement of transmission or scatter of X-rays or γ-rays at a different energy so chosen that there is a significant difference in absorption of radiation per unit weight of coal matter and mineral matter and that the relative absorption per unit weights by said coal matter and said mineral matter at any one energy is significantly different from the relative absorption at each other energy including said first energy.

2. A method as defined in claim 1 wherein the step (ii) is constituted by transmission or scatter of X-rays or γ-rays at one further energy chosen that there is a significant difference in absorption of radiation per unit weight in coal matter and mineral matter and that the relative absorption per unit weights by said coal matter and said mineral matter at said first energy is significantly different from the relative absorption at said second energy.

3. The method wherein the concentration of ash or mineral matter in coal or coke is determined as defined in claim 2 coupled with a further measurement of iron concentration by neutron capture γ-ray techniques.

4. The method as defined in claim 1 wherein the concentration of ash or mineral matter in coal or coke is determined from the result of a measurement of iron concentration by neutron capture γ-ray techniques, combined with the measurement of transmission or scatter of X-rays or γ-rays at an energy chosen such that there is a significant difference in absorption of radiation per unit weight in coal matter and mineral matter excluding iron.

5. The method wherein the concentration of ash or mineral matter in coal or coke is determined as defined in claim 1 coupled with one or more additional measurements selected from (i) measurement of weight per unit area or a measurement proportional thereto, or (ii) measurement of bulk density.

6. The method defined in claim 5 wherein the weight per unit area is determined from the result of a measurement of the transmission or scatter of X- or γ-rays.

7. The method wherein the concentration of ash or mineral matter in coal or coke is determined as defined in claim 1 coupled with a measurement of moisture or hydrogen content.

(viz. neutron scatter or transmission, or capture γ-rays from neutron absorption by hydrogen).

The method as described in the first and second forms of the present invention also partly compensates for variable amounts of other elements, e.g., calcium or sulphur in the mineral matter which have a high mass absorption coefficient compared with the mean for the other mineral matter constituents and hence improves accuracy of analysis for content of mineral matter and hence ash.

Because of better sensitivity to variations in ash content X- or low energy γ-ray transmission measurements are usually preferred to X- or γ-ray scatter. However, it is possible using scatter to determine the ash content of coal in the ground, e.g., in a borehole.

The method of the invention may be carried out on coal on a conveyor, in a chute, or in a pipe. The coal may be dry or in a slurry and can be in coarse lumps or finely divided. It is convenient and preferred to apply the method of the invention to a continuous monitoring of ash content of coal but the invention is not so restricted as the method can also be applied to discrete samples of coal.

The energies of the X- and low energy γ-rays are chosen in relation to the particular analysis application. For example, in the use of X- and low energy γ-ray transmission to determine the ash content of coal on a conveyor belt, the X-ray energies are chosen so that high absorption of X-rays in the thickness of coal occurs and consequently high sensitivity to changes in ash content, but sufficient transmission of X-rays through the coal occurs so that the transmitted X-ray intensities can be accurately measured.

Some suitable radioisotopes which may be used as sources of the X- and low energy γ-rays with the method of the invention are Am-241, Gd-153, Cd-109, Cm-244, Pu-238 and Co-57. As well as using their direct radiation the above sources may be used with a secondary target to produce a range of intermediate energy radiation as described in Watt J.S., "γ-ray excited X-ray sources" International Journal of Applied Radiation and Isotopes, 1964, Vol. 15 P 617. Some radioisotopes which may be used as sources of γ-rays are Ba-133, Cs-137 and Co-60. Some radioisotope sources of neutrons are Cf-252, Pu-238/Be and Am-241/Be. As well as radioisotope sources, other possible sources of X-rays and neutrons are X-ray tubes and neutron generators but these are considerably more complex and expensive.

In the case of continuous monitoring, the radioisotope sources and detectors are preferably placed in a line parallel to the direction of movement of the coal to ensure that the coal seen by each source-detector system is approximately the same.

When the method of the invention is used to determine ash in coal on a conveyor belt it may in some cases be necessary to compensate for slight variations in belt thickness by continuously measuring the thickness of the belt. This could be achieved by conventional radioisotope techniques on the empty return section of the belt.

DESCRIPTION OF PREFERRED EMBODIMENTS

Preferred embodiments of the invention are described in the following examples with reference to the drawings.

EXAMPLE 1

Figure 1:
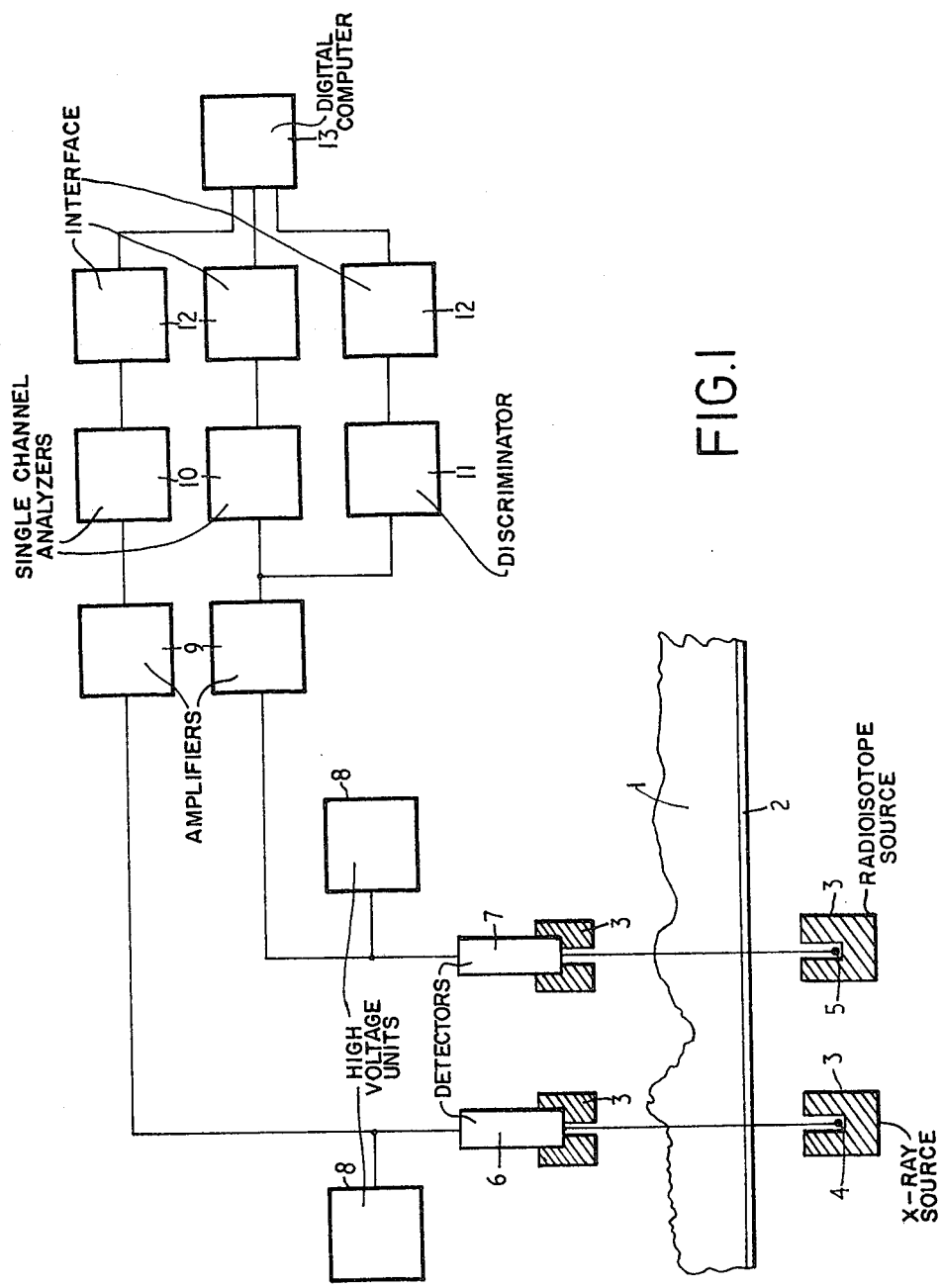
FIG. 1 is a diagrammatic illustration of a first embodiment according to the invention.

In FIG. 1, coal 1 on a moving conveyor belt 2 is viewed by two beams of X- or γ-rays collimated by lead shields 3 so that X- and γ-rays scattered by the coal have little probability of being seen by the detectors. The first beam is provided by a source 4 of X-rays having an energy of about 30 keV and is detected by a scintillation detector 6. The second beam is provided by Ba-133 and Am-241 radioisotope sources 5 and is detected by a second scintillation detector 7. Ba-133 emits γ-rays at 356 keV and others and Am-241 emits γ-rays at 59,5 keV. A small shield is placed about the Ba-133 source to reduce considerably the intensity of low energy (less than 100 keV) Ba-133 γ-rays detected by scintillation detector 7 and thus enhancing the selectivity to detection of 59,5 keV γ-rays.

The electronics used with the scintillation detectors 6, 7 are known art and comprise high voltage units 8 to polarise the scintillation detectors 6, 7, amplifiers 9, single channel analysers 10 or discriminator 11 to select electrical pulse heights corresponding to the appropriate γ- or X-rays detected, and interface units 12 to link outputs from units 10, 11 with the digital computer 13 which scales the electrical pulses and calculates ash content.

EXAMPLE 2

Figure 2:
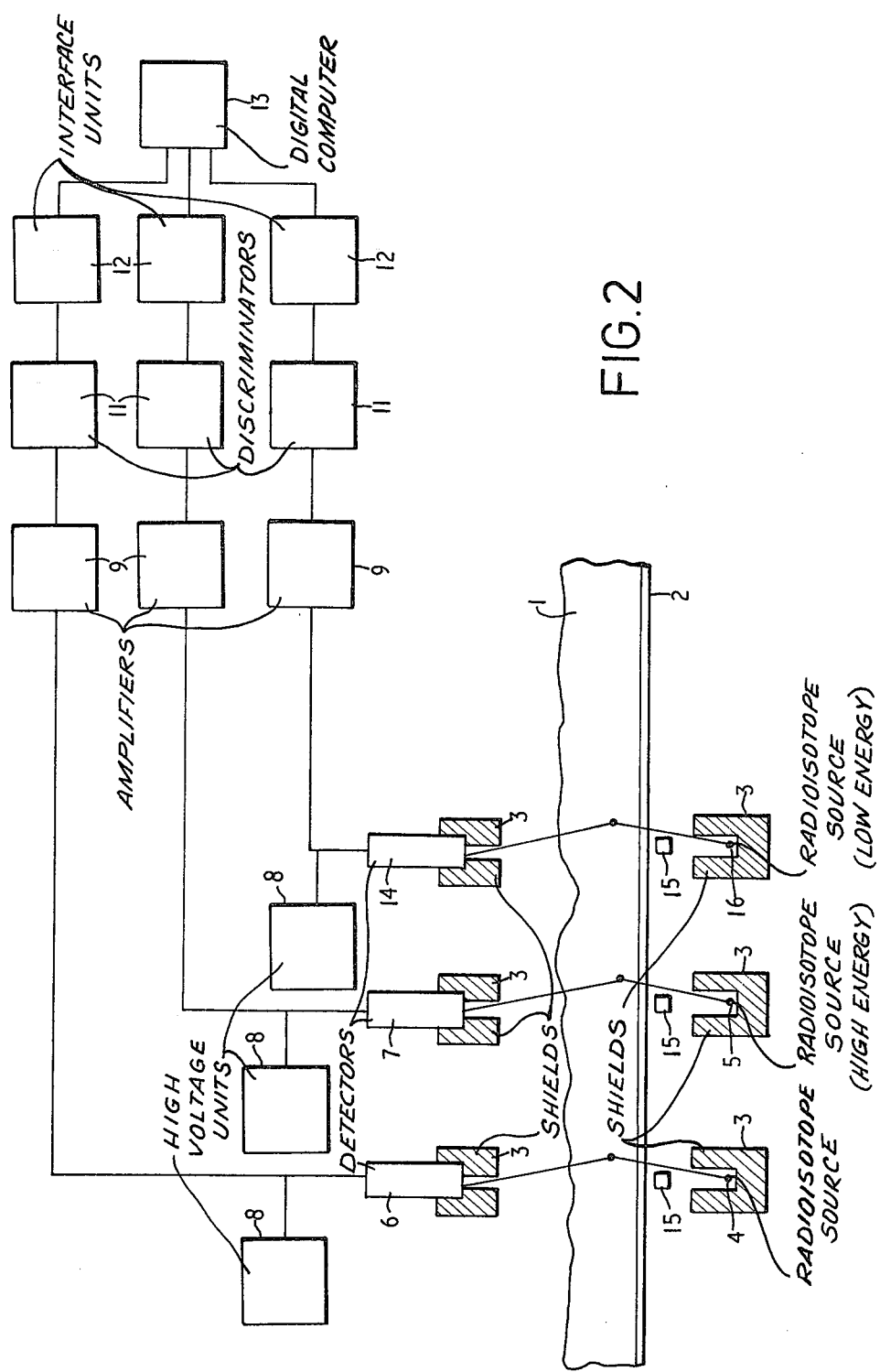
FIG. 2 is a diagrammatic illustration of a second embodiment according to the invention.
Figure 3:
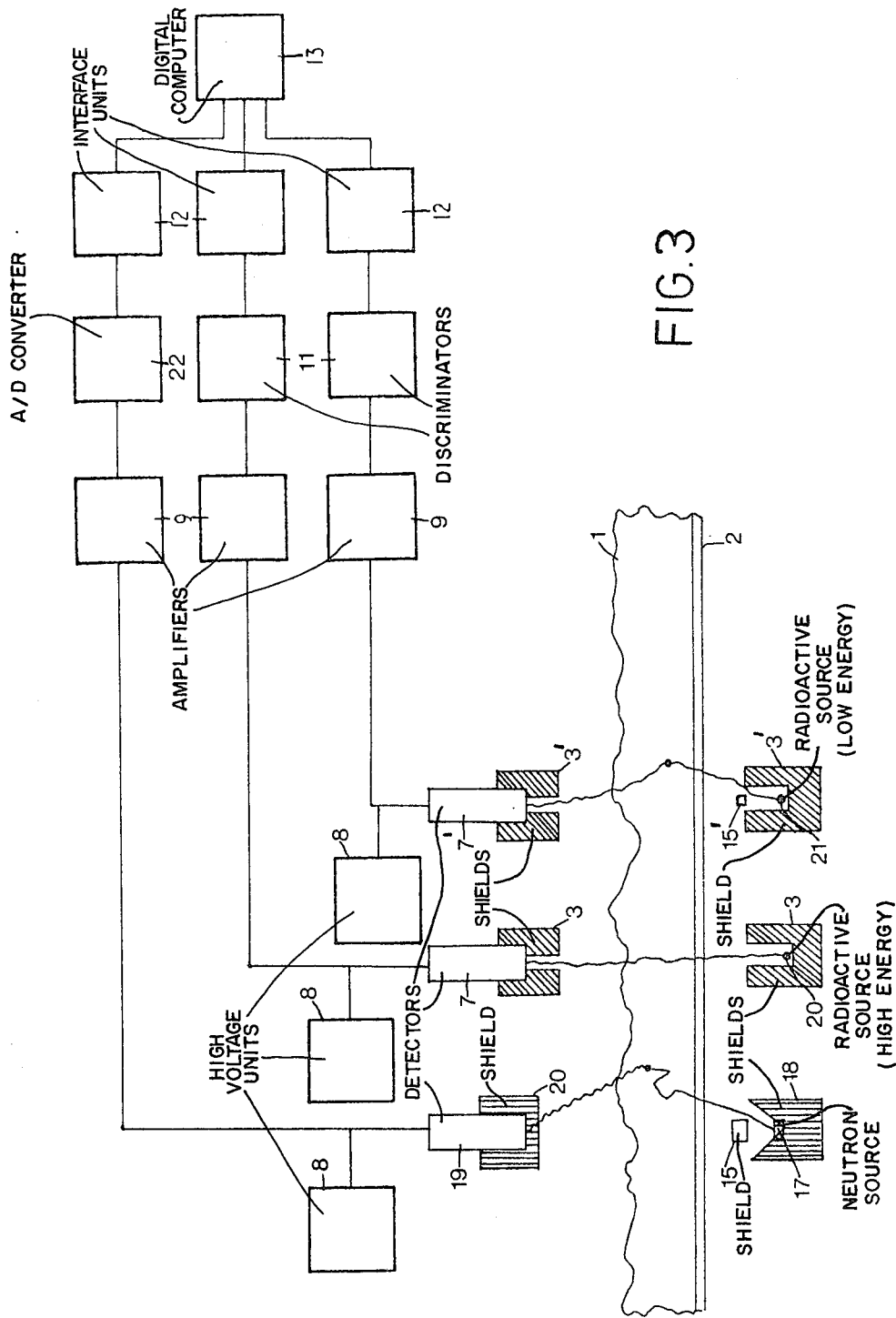
FIG. 3 is a diagrammatic illustration of a third embodiment according to the invention.

In FIG. 2, three beams of X- and/or γ-rays interact with coal 1 on a moving conveyor belt 2 and some of the resultant scattered rays are detected by scintillation detectors 6, 7, 14. Shields 15 placed between each source-detector pair 4, 6, 5, 7, 16, 14 prevent unscattered X- and γ-rays from being detected. The first beam is provided by a source of X-rays 4 having an energy of about 30 keV and is detected by a scintillation detector 6. The second beam is provided by an Am-241 radioisotope source 5 which emits 59,5 keV γ-rays, and is detected by a second scintillation detector 7. The third beam is provided by a Ba-133 radioisotope source 16 which emits γ-rays at 356 keV and other energies, and is detected by a third scintillation detector 14. Each radioisotope source and detector is partly collimated by lead shielding 3, and spaced apart, to ensure that each scintillation detector detects essentially only X- or γ-rays from the radioisotope source corresponding to it. In some cases, it will be advantageous to have the Ba-133 γ-rays collimated at source and detector but with no shield 15, so that essentially narrow beam conditions hold.

The electronics used with the scintillation detectors 6, 7, 14 are known art and comprise high voltage units 8 to polarise the scintillation detectors 6, 7, 14, amplifiers 9, discriminators 11 to differentiate signal from noise, and interface units 12 to link outputs from units 11 with the digital computer 13 which scales the electrical pulses and calculates ash content.

EXAMPLE 3

The determination of ash content of coal using transmission of one low energy γ-ray beam and one high energy γ-ray beam combined with neutron capture 8. The method as defined in claim 7 wherein the moisture or hydrogen content is measured by neutron scatter or transmission, or capture γ-rays from neutron absorption by hydrogen.

9. The method as defined in claim 1 wherein the X- or γ-rays are obtained from Am-241, Gd-153, Cd-109, Cm-244, Pu-238 and/or Co-57.

10. A method of analyzing coal or coke comprising determining the concentration of ash or mineral matter in coal or coke by the steps comprising (i) measuring transmission or scatter of X-rays or γ-rays of a first energy chosen such that there is significant difference in absorption of radiation per unit weight in coal matter and mineral matter excluding iron, in combination with (ii) effecting measurement of iron concentration by neutron capture γ-ray techniques.

11. The method wherein the concentration of ash or mineral matter in coal or coke is determined as defined in claim 10 coupled with one or more additional measurements selected from (i) measurement of weight per unit area or a measurement proportional thereto, or (ii) measurement of bulk density.

12. The method defined in claim 11 wherein the weight per unit area is determined from the result of a measurement of the transmission or scatter of X- or γ-rays.

13. The method wherein the concentration of ash or mineral matter in coal or coke is determined as defined in claim 10 coupled with a measurement of moisture or hydrogen content.

14. The method as defined in claim 13 wherein the moisture of hydrogen content is measured by neutron scatter or transmission, or capture γ-rays from neutron absorption by hydrogen.

15. The method as defined in claim 10 wherein the neutrons are obtained from Cf-252, Pu-238/Be and/or Am-241/Be.

* * * * *